United States Patent [19]

Johnson

[11] Patent Number: 5,354,343

[45] Date of Patent: Oct. 11, 1994

[54] GASOLINE COMPOSITION

[75] Inventor: Thomas H. Johnson, Houston, Tex.

[73] Assignee: Shell Oil Company, Houston, Tex.

[21] Appl. No.: 156,525

[22] Filed: Nov. 19, 1993

Related U.S. Application Data

[63] Continuation-in-part of Ser. No. 938,914, Aug. 31, 1992, abandoned.

[51] Int. Cl.$^5$ .................... C10L 1/22; C07C 217/42
[52] U.S. Cl. ............................... 44/433; 564/508; 564/346; 564/505
[58] Field of Search ............ 564/508, 346, 505; 44/433; 252/51.5 R; C10L 1/22

[56] References Cited

U.S. PATENT DOCUMENTS

| | | |
|---|---|---|
| 2,166,152 | 7/1939 | Howk . |
| 2,166,183 | 7/1939 | Signaigo . |
| 2,305,673 | 12/1942 | Chenicek ........................ 44/433 |
| 2,683,659 | 7/1954 | Schlesinger et al. . |
| 3,169,991 | 2/1965 | Rogier . |
| 3,236,895 | 2/1966 | Lee et al. . |
| 3,255,253 | 6/1966 | Kuryla . |
| 3,372,195 | 3/1968 | Little . |
| 3,382,032 | 5/1968 | Cox ........................ 564/508 |
| 3,440,029 | 4/1969 | Little et al. . |
| 3,544,615 | 12/1970 | Poppelsdorf . |
| 4,168,242 | 9/1979 | Soula . |
| 4,235,821 | 11/1980 | Butte, Jr. et al. . |
| 4,240,804 | 12/1980 | Shields . |
| 4,252,746 | 2/1981 | Kwong . |
| 4,259,262 | 3/1981 | Drake . |
| 4,279,621 | 7/1981 | Reusser . |
| 4,298,352 | 11/1981 | Blysing ........................ 44/433 |
| 4,534,910 | 8/1985 | Peeters et al. . |
| 4,604,103 | 8/1986 | Campbell . |
| 4,877,416 | 10/1989 | Campbell . |
| 4,985,047 | 1/1991 | Sung et al. . |
| 5,053,152 | 10/1991 | Steckel . |
| 5,213,584 | 5/1993 | Izaiku et al. ........................ 44/433 |

FOREIGN PATENT DOCUMENTS

| | | |
|---|---|---|
| 604467 | 8/1960 | Canada . |
| 0100665 | 2/1984 | European Pat. Off. . |
| WO85/00827 | 2/1985 | European Pat. Off. . |
| 1205548 | 11/1965 | Fed. Rep. of Germany . |
| 1804361 | 5/1970 | Fed. Rep. of Germany . |
| 491401 | 3/1954 | Italy . |

Primary Examiner—Prince Willis, Jr.
Assistant Examiner—Alan D. Diamond
Attorney, Agent, or Firm—Timothy J. Hadlock

[57] ABSTRACT

The invention includes a compound of formula I

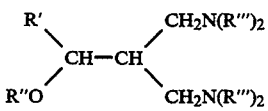

where R' is hydrogen, an alkyl, or aryl group; R"O is derived from R"OH which is a polyether mono-ol or hydrocarbyl mono-ol; and R''' independently is a hydrogen, an alkyl group or a substituted alkyl group. The invention also includes an unleaded fuel composition containing a compound of formula I and a process for making the compound of formula I.

3 Claims, No Drawings

GASOLINE COMPOSITION

This application is a continuation-in-part of application Ser. No. 07/938,914 filed Aug. 31, 1992, now abandoned.

FIELD OF THE INVENTION

The present invention relates to gasoline compositions for reducing intake valve deposits in port fuel injected engines.

BACKGROUND OF THE INVENTION

Gasoline compositions have traditionally been formulated to improve the performance of carburetor and throttle body injected engines. Beginning in about 1984, electronic port fuel injected engines were commonly introduced by automobile manufacturers. Shortly thereafter, in about 1985, problems began to be reported with intake valve deposits in electronic port fuel injected engines, which problems are characterized by hard starting, stalls, and stumbles during acceleration and rough engine idle.

Conventional commercial gasoline additives contain nitrogen. The nitrogens are attached to a polymer, and the nitrogens are separated by two or three carbons. This structure provides a potential for chelation. However, steric hinderance reduces chelatability in conventional additives since the polymer is attached through one of the nitrogen atoms.

Without limiting the invention by theories of operation, it has now been discovered that chelatability is advantageous for its deposit reducing tendencies. Accordingly, it would be desirable to have a new gasoline additive for unleaded fuel compositions which have increased chelatability and thus reduce or eliminate undesirable intake valve deposits in electronic port fuel injected engines. Also, since some carburetor and throttle body injector engines will still be in use for the foreseeable future, it would be desirable if such fuels could also be compatible with these engines.

SUMMARY OF THE INVENTION

It has now been found that an intake valve deposite reducing additive can be made which has increased chelatability by attaching the polymer separated from the chelating atoms, i.e., nitrogens.

The invention includes a compound of formula I

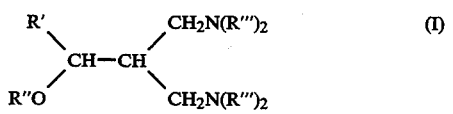

where R' is hydrogen, an alkyl group of from 1 to 20 carbons, or aryl group, including an akylaryl group; R"O is derived from R"OH which is a polyether mono-ol or hydrocarbyl mono-ol; and R''' independently is a hydrogen, an alkyl group, or a substituted alkyl group.

The invention also includes an unleaded fuel composition containing a major amount of a hydrocarbon base fuel of the gasoline boiling range containing an amount effective to reduce formation of deposits in electronic port fuel injected engines when combusted in said engines of a compound of formula I above.

The invention also includes a process for preparing a gasoline additive compound if formulated by reacting a dinitrile compound of formula II

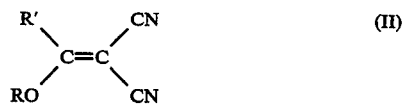

with a polyether mono-ol or hydrocarbyl mono-ol of formula R"OH to produce an intermediate compound of formula III

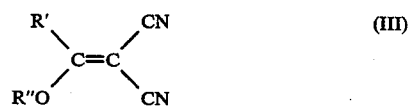

and hydrogenating said intermediate compound to produce a diamine of formula IV

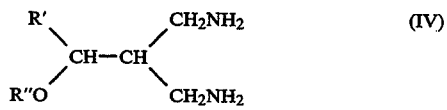

where R' and R" have the meanings defined above and R is an alkyl group.

DETAILED DESCRIPTION OF THE INVENTION

Compound

One aspect of the invention is a compound of formula I

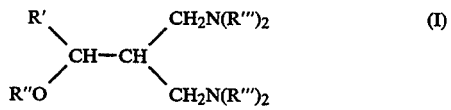

R' and R"O are defined above. R''' independently is a hydrogen, an alkyl group, or a substituted alkyl group. R''' is preferably hydrogen.

R"OH is preferably an oil soluble poly(oxyalkylene) polyether of the formula $R_1$—O—$(R_2O)_n$—H wherein $R_1$ represents an aliphatic, including cycloaliphatic, or aromatic hydrocarbon radical containing up to about 40 carbon atoms, $R_2$ represents an alkylene radical containing up to about 12 carbon atoms, and n is an integer of at least 7.

R"OH is more preferably of the formula $R_1O$—(EO)$_a$—(PO)$_b$—(BO)$_c$—(XO)$_d$—H wherein $R_1$ represents an aliphatic, cycloaliphatic or aromatic hydrocarbon radical containing up to 40 carbon atoms, and where EO is a moiety resulting from a ring-opening of ethylene oxide, PO is a moiety resulting from a ring-opening of propylene oxide, BO is a moiety resulting from a ring-opening of butylene oxide, XO is a moiety resulting from a ring-opening of a hydrocarbon oxide having from about five to about 16 carbons, a, b, c, and d are each from 0 to 100, and the sum of a, b, c, and d is at least 7. In this form of R"OH, a, b, and d each are preferably 0 and c is from about 10 to about 40. More preferably, $R_1O$ is a moiety resulting from a ring opening of butylene oxide.

In another preferred form R"O is derived from a polyether mono-ol where $R_1$ is preferably a butyl or a $C_{12}$ to $C_{18}$ alkyl group and n is from about 10 to about 40, i.e., $C_{12}H_{23}O$—$C_{18}H_{37}O(C_4H_8O)_nH$; or $C_4H_9O(C_4H_8O)_nH$, where n is from about 10 to about 40, and mixtures thereof. Of this group R"O more preferably is derived from $C_4H_9O(C_4H_8O)_nH$, where n is from about 10 to about 40.

Preferably, the polyether has a number average molecular weight not more than about 5000. More preferably, the polyether has a number average molecular weight from about 500 to about 3000. Where R"O is derived from $C_4H_9O(C_4H_8O)_nH$, R"O preferably has a number average molecular weight of from about 1900 to about 2100. In the compound of formula I preferably R' is H, R"O is polyloxybutlene, and R''' is H.

Where R"O is derived from a hydrocarbyl mono-ol R"OH is a linear or branched alkanol or alkenol of the formula $CH_3(CH_2)_nOH$ or corresponding alkenol, where n is a number from about 1 to about 140. A preferred branched alkenol is polyisobutylene mono-ol. The desired molecular weight of R"O when R"O is derived from a hydrocarbyl mono-ol is the same as given above where R"O is derived from a polyether mono-ol. Thus, "n" is set so as to place R"O in the desired molecular weight range.

Fuel Composition

Another aspect of the invention is an unleaded fuel composition. The fuel composition contains a major amount of a hydrocarbon base fuel of the gasoline boiling range. As used in this specification and appended claims the term "major" means greater than 50% wt. The fuel composition also contains an amount of a compound of formula I effective to reduce formation of deposits in electronic port fuel injected engines when combusted in said engines.

When used in a fuel composition the compound of formula I is present in the fuel preferably in a quantity of about 75 ppmw or higher based on the fuel composition. The compound of formula I is optionally admixed with at least one carrier component. Carriers include (i) a copolymer of a $C_2$ to $C_6$ monoolefin; (ii) an oil soluble poly(oxyalkylene) alcohol, glycol or polyol or mono or di ether thereof; or (iii) a polyalphaolefin having a viscosity at 100° C. of from about 2 to about 20 centistokes.

These polymeric carriers for use with the compound of the invention are individually well known in the art and patents related to their manufacture and use include, e.g., U.S. Pat. Nos. 2,692,257, 2,692,258, 2,692,259, 2,918,508 and 2,970,179, and their disclosures are incorporated herein by reference.

The copolymers of monoolefins which are employed in the motor fuel of the invention are characterized by a number average molecular weight by osmometry in the range from about 500 to about 1900 and preferably from about 550 to about 1500. Particularly preferred are those having an average molecular weight in the range from about 600 to about 950. Mixtures of polymers wherein a substantial portion of the mixture has a number average molecular weight above 1500 may be less effective. The polyolefins may be prepared from unsaturated hydrocarbons having from two to six carbon atoms including, e.g., ethylene, propylene, butylene, isobutylene, butadiene, amylene, isoprene, and hexene and the like.

Preferred for their efficiency and commercial availability are copolymers of propylene and butylene; particularly preferred are polymers of isobutylene. Also suitable and part of this invention are derivatives resulting after hydrogenation of the above polymers.

The polyoxyalkylene is the preferred carrier of the invention. It can be a polyoxyalkylene compound of the formula $R_1$—O—$(R_2O)_n$—$R_3$ wherein $R_1$ and $R_3$ each independently represents a hydrogen atom or an aliphatic, cycloaliphatic or aromatic hydrocarbon radical containing up to about 40 carbon atoms, $R_2$ represents an alkylene radical containing up to about 12 carbon atoms, and n represents an integer of at least about 7, preferably at least about 20 when $R_2O$ is a 1,2-propylene group. In the polyoxyalkylene chain—$(R_2O)_n$—, the group $R_2$ is an alkylene radical. The polyoxyalkylene chain optionally contains two or more dissimilar alkylene groups, which preferably are alkylene radicals of 2 to 8 carbon atoms, especially ethylene or 1,2-propylene groups. These groups are optionally distributed randomly throughout the chain or arranged in a predetermined pattern of units or blocks, each containing one or a plurality of oxyalkylene radicals.

In one embodiment of the invention, at least one of $R_1$ and $R_3$ is an alkyl or alkylphenyl group containing up to about 20 carbon atoms, for example, propyl, butyl, pentyl, hexyl, octyl, nonyl, decyl or dodecyl, or octylphenyl, or nonylphenyl. Preferably, $R_1$ is hydrogen and $R_3$ is an alkyl group, more preferably, $R_3$ is dodecyl or a mixture of alkyls from $C_{12}$ or $C_{15}$.

Suitable carriers include polyoxypropylene glycols and the glycols containing both ethylene and 1,2-propylene groups in the polyoxyalkylene chain as well as the mono- and di-alkyl ethers of such glycols.

The commercially available polyoxyalkylene compounds are generally mixtures of compounds in which the values for n and the molecular weight of such mixtures are only average values. The values of n of typical compounds are usually from about 7 to about 100, preferably from about 8 to about 80. The molecular weights vary from about 400 to about 6000, preferably from about 500 to about 4000 and more preferably from about 1000 to about 2000.

When the component (b) is a polyalphaolefin it has a viscosity at 100° C. of from about 2 centistokes to about 20 centistokes. Such polyalphaolefins are suitably hydrogenated oligomers derived from alphaolefinic monomers containing at least 6 carbon atoms. The hydrogenated oligomer itself preferably contains from about 18 to about 80 carbon atoms. Preferably the monomer contains from 6 to 24 carbon atoms and especially 8 to 12 carbon atoms, while the oligomer preferably contains about 30 to about 80 carbon atoms. The preparation of these oligomers is described in *Hydrocarbon Processing*, February 1982, beginning at page 75.

Mixtures, usually of equal amounts, of more than one kind of carrier can be used. The component (b) is preferably a polyoxyalkylene alcohol, glycol or polyol and especially an ether thereof to help prevent low temperature intake valve sticking. Such a component is preferably used at about 75 to about 175 ppmw, and especially at about 125 ppmw based on the fuel composition.

Suitable liquid hydrocarbon fuels of the gasoline boiling range are mixtures of hydrocarbons having a boiling range of from about 25° C. (77° F.) to about 232° C. (450° F.) and comprise mixtures of saturated hydrocarbons, olefinic hydrocarbons and aromatic hydrocarbons. Preferred are gasoline blends having a saturated hydrocarbon content ranging from about 40 to about 80 percent volume, an olefinic hydrocarbon content from 0 to about 30 percent volume and an aromatic hydrocarbon content ranging from about 10 to about 60 percent volume. The base fuel is optionally derived, for example, from straight run gasoline, polymer gasoline, natural gasoline, dimer or trimerized olefins, synthetically produced aromatic hydrocarbon mixtures from thermally or catalytically reformed hydrocarbons, or from catalytically cracked or thermally cracked petroleum stocks, or mixtures of these. The hydrocarbon composition and octane level of the base fuel are not critical. The octane level, (R+M)/2, will generally be above 85. Any conventional motor fuel base may be employed in the practice of this invention. For example, in the gasoline, hydrocarbons can be replaced by up to substantial amounts of conventional alcohols or ethers conventionally known for use in fuels. The base fuels are desirably substantially free of water, since water impedes a smooth combustion.

Normally, the hydrocarbon fuel mixtures to which the invention is applied are essentially lead-free, but can contain minor amounts of blending agents such as methanol, ethanol, methyl tertiary butyl ether, and the like, e.g., at from about 0.1 to about 15% volume of the base fuel. The fuels can also contain antioxidants such as from 1 ppmw to 40 ppmw, based on the fuel composition. The fuels also optionally contain, phenolics, e.g., 2,6-di-tert-butylphenol, or phenylenediamines, e.g., N,N'-di-sec-butyl-p-phenylenediamine, dyes, metal deactivators, dehazers such as polyester-type ethoxylated alkylphenol-formaldehyde resins and the like. Corrosion inhibitors, such as a polyhydric alcohol ester of a succinic acid derivative having on at least one of its alpha-carbon atoms an unsubstituted or substituted aliphatic hydrocarbon group having 20 to 500 carbon atoms, for example, pentaerythritol diester of polyisobutylene-substituted succinic acid, the polyisobutylene group having an average molecular weight of about 950, in an amount of about 1 to 1000 ppmw. The fuels may also contain antiknock compounds such as a methyl cyclopentadienylmanganese tricarbonyl or ortho-azidophenol. The gasoline can also contain a dehazer, particularly a polyester-type alkoxylated alkylphenol-formaldehyde resin. The additives of the present invention can be introduced into the combustion zone of the engine in a variety of ways to prevent buildup of deposits, or to accomplish reduction or modification of deposits. Thus, the additives are injected into the intake manifold intermittently or substantially continuously, preferably in a hydrocarbon carrier having a final boiling point (by ASTM D86) lower than about 232° C. (450° F.). A preferred method is to add the additives to the fuel. For example, the agent can be added separately to the fuel or blended with the other fuel additives.

Process to Make

Another aspect of the invention is a process for preparing the gasoline additive compounds of formulas IV and of formula I above. The compound of formula IV is prepared by reacting a dinitrile compound of formula II, where R is an alkyl group,

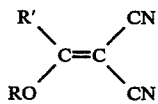 (II)

with a polyether mono-ol or hydrocarbyl mono-ol of formula R"OH to produce an intermediate compound of formula III

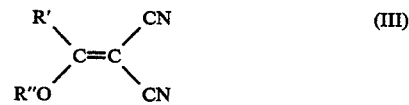 (III)

The reaction is at atmospheric pressure and at a temperature sufficient to maintain evolution of ROH, e.g., ethanol where R is an ethyl group. Preferably, the temperature is from about 100° C. to about 140° C. The reaction is preferably done in a batch process and reaction occurs for a time sufficient to obtain the desired amount of conversion, e.g., from about 4 to about 5 hours. The dinitrile compound of formula II is preferably reacted with R"OH in the presence of a catalyst such as $ZnCl_2$. Where the catalyst is zinc chloride, a solvent in which zinc chloride is soluble is also added to the reaction mixture. Such a solvent includes methanol, ethanol, isopropanol, and other lower alcohols which will distill off after the reaction in a reasonable time period at under about 110° C. The solvent need not be premixed with the zinc chloride. A typical ratio of solvent to zinc chloride is about 10:1 by weight or greater. Where a solid catalyst other than zinc chloride is used, a suitable solvent is chosen in which the catalyst will dissolve and will distill off after the reaction in a reasonable time period at under about 110° C.

An alternate route for forming the compound of formula III is substituting the ethoxymethylene malononitrile of the above route with equimolar quantities of malononitrile and triethyl orthoformate. Thus this alternate reaction to produce the compound of formula II is a follows: R"OH is reacted with

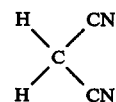

and $(RO)_3OH$ where R is an alkyl. The reaction conditions are the same as for the first reaction method above.

The intermediate compound of formula III is then hydrogenated to produce a diamine of formula IV

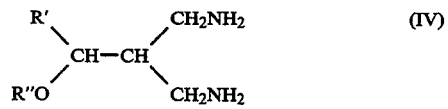 (IV)

The R', R"O, and R"OH groups are described in various forms including preferred forms earlier in this specification. The hydrogenation is accomplished, for example, by reaction with a metal hydride such an aluminum hydride at atmospheric pressure and ambient temperature. Sub-ambient temperatures are preferred where the reaction is exothermic.

Alternately, the hydrogenation is achieved by contact with hydrogen gas at elevated pressures in the presence of a hydrogenation catalyst such as a Raney cobalt or Raney nickel catalyst. Hydrogen pressures for use with such Raney catalysts are, e.g., from about 2000 psi to about 3000 psi. Temperatures are preferably from about 80° C. to about 150° C.

The compound of formula I is then prepared by further reaction of the compound of formula IV. The diamine of formula IV is reacted with (R''')X, where X is a halogen, to produce the compound of formula I

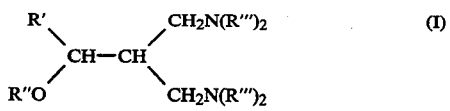

In formula I R', R''O, and R''' are as previously described above. The reaction conditions are atmospheric pressure and from ambient temperature to about 100° C.

The invention will now be illustrated with reference to the following illustrative embodiments which should not be regarded as limiting the invention in any way.

ILLUSTRATIVE EMBODIMENTS

Illustrative Embodiment A—Composition Preparation

Preparation of 2-Poly(oxybutylene)-1,1-di(methyleneamino)ethane, i.e., the compound of formula IV above where R' is H, R''O is a moiety resulting from the ring opening of butylene oxide, and R''' is H. The method of preparation was as follows:

A. First Step, Method 1

Poly(oxybutylene) used in this embodiment had a molecular weight of 1000, 1500, and 2000, as used in separate runs, respectively. The engine test results of the compounds resulting from these separate runs are given below in Table 1. Poly(oxybutylene) from Dow and ethoxymethylene malononitrile from Aldrich were mixed in a 1:1.02 molar ratio as a 50% xylene solution which also contains 0.08–0.2 wt % zinc chloride, and 1 wt % (based on the poly(oxybutylene)) ethanol. The reaction temperature was maintained at a level sufficient to sustain ethanol evolution, typically from about 100° C. to about 140° C. The reaction was complete with no further ethanol evolution after from about four to about five hours. The reaction was allowed to cool to room temperature whereupon zinc chloride was filtered off and xylene stripped to obtain solvent-free material for analysis. Analysis by NMR revealed about 100% of the poly(oxybutylene) was terminated with the dinitrile functional group.

B. First Step, Method 2

This alternate reaction was performed identically to method 1 above except that ethoxymethylene malononitrile was replace by equimolar quantities of malononitrile and triethyl orthoformate. The amount of ethanol evolved was increased to three equivalents per equivalent of poly(oxybutylene).

C. Second Step—Hydrogenation

1:1 (v/v) solution of 2-poly(oxybutylene) -1,1-dinitriloethene in dry toluene was reduced with commercial Na$_2$AlH$_2$(OCH$_2$CH$_2$OCH$_3$)$_2$ (70% in toluene). Due to the exothermicity of the reaction, external cooling was employed. The product of the reaction was neutralized using an equimolar equivalent of 15% NaOH followed by quench with water. Conventional separation and drying provided the product.

Illustrative Embodiment A'—Composition Preparation Where R''O is Derived From a Hydrocarbyl Mono-ol Where R''O is derived from a hydrocarbyl mono-ol, the procedure is the same as given in Illustrative Embodiment A above, except that the R''O derived from a hydrocarbyl mono-ol is substituted for the poly(oxybutylene).

Illustrative Embodiment B—Engine Tests

Fuels with and without the additive of the instant invention were tested in a 3.3 liter Dodge engine with Port Fuel Injection (PFI), V-6 for 100 hours to determine the effectiveness of the instant additives in reducing intake valve deposits.

The base fuel comprised premium unleaded gasoline. The diamine compound prepared as noted in Illustrative Embodiment A was used as the intake valve reducing additive except that the number average molecular weight of the poly(oxybutylene) varied as indicated in Table 1. No carrier was used except unreacted reactants resulting from incomplete reaction during preparation of the additive. Each additive was added to the gasoline in a concentration of 125 ppm active matter, i.e., 125 ppm diamine and some remaining unreacted reactants.

Each engine was in clean condition at the start of the test, i.e., oil and filters were changed and all deposits had been removed from the intake manifolds, intake ports and combustion areas of the engine. In order to test for the accumulation of deposits in the engine during each test, the engines were operated on a cycle consisting of idle mode and cruising modes of 30, 35, 45, 55 and 65 miles an hour with acceleration and decelerations. The tests were conducted for 100 hours and the weight of the intake value deposits was measured. Results of these tests are set forth in Table 1 below.

TABLE 1

| Intake Valve Deposits for Diamine Additive of Formula I | | | |
|---|---|---|---|
| Additive | | | Average Deposit Weight |
| R' | R''' | R''O | Per Valve, mg |
| | | None (base fuel) | 188 |
| H | H | Poly 80 (1000 MW) | 95 |
| H | H | Poly 80 (1500 MW) | 56 |
| H | H | Poly 80 (2000 MW) | 22 |

Results of these tests demonstrate that the composition of the invention is very useful in very significantly preventing the accumulation of deposits in the engines tested as compared to the effects of the base fuel as shown by the much lower average valve deposits. The 2000 MW poly BO additive has particularly good performance.

Illustrative Embodiment C—BMW Engine Tests

Intake valve detergency is generally measured by the BMW NA standard of intake valve cleanliness for unlimited mileage, which is an established correlation of driveability and intake valve deposit weight of 100 milligrams or less. Intake valve deposit tests were conducted at Southwest Research Institute in 1985 model BMW 318i cars equipped with the 1.8-liter, four-cylinder engine, and were operated for 10,000 miles on the test fuel. Before the test started, deposits were removed from the cylinder head, intake manifold and piston tops and new intake valves were weighed and installed. The oil and filter were changed, new spark plugs installed and the fuel injectors flow checked. Mileage was accumulated on public roads using trained drivers. The test route consisted of about 10% city driving, 20% on secondary roads and 70% highway driving (maximum speed of 65 mph).

The primary test data are the intake valve deposit (IVD) weights at the end of the 10,000-mile test. IVD weights are also determined at 5,000 miles, where tests can be terminated if the results are not promising. BMW's pass criteria are as follows: an average deposit weight of 100 milligrams per valve or less at the conclusion of the test meets BMW requirements for unlimited mileage acceptance: an average deposit weight of 250 mg per valve or less at the conclusion of the test meets BMW requirement for 50,000-mile service.

Table 2 below lists the additive composition used in premium unleaded base gasolines and the average intake valve deposit weight at the end of the test (10,000 miles).

TABLE 2

BMW TEST

| Composition | | Ave. Deposit Per Valve |
|---|---|---|
| (a)[1] | (b)[2] | |
| 172 ppmw | 28 ppmw | 46 mg |

[1]Component "a" is the compound of formula I where R' was H, R''' was H, and R"O was derived from $C_4H_9O(C_4H_5O)_nH$, where n was from about 10 to about 40 and wherein R"O had a number average molecular weight of about 2000.
[2]Component "b" was unreacted reactants from dinitrile preparation, primarily R"OH.

Results of this test demonstrates that the gasoline composition of the invention passes the BMW unlimited mileage test with low deposits.

What is claimed is:

1. A compound of formula I

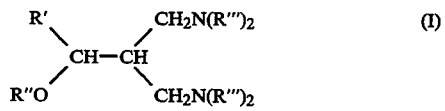

where R' is hydrogen, an alkyl, or aryl group; R"O is derived from R"OH which is a polyether mono-ol or hydrocarbyl mono-ol; and R''' is hydrogen.

2. The compound of claim 1 wherein the compound of formula I, R' is an alkyl group having a carbon number from about 1 to about 20 and R"O is derived from $C_4H_9O(C_4H_8O)_nH$, where n is from about 10 to about 40.

3. An unleaded fuel composition comprising a major amount of a hydrocarbon base fuel of the gasoline boiling range containing an amount effective to reduce formation of deposits in electronic port fuel injected engines when combusted in said engines of a compound of the formula

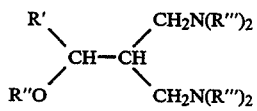

where R' is hydrogen, an alkyl, or aryl group; R"O is derived from R"OH which is a polyether mono-ol or hydrocarbyl mono-ol; and R''' is hydrogen.

* * * * *